(12) United States Patent
Mackool

(10) Patent No.: US 9,387,122 B2
(45) Date of Patent: Jul. 12, 2016

(54) MONITORING THERMAL CONDITIONS TO VARY OPERATION OF AN ULTRASONIC NEEDLE TIP OF A SURGICAL INSTRUMENT

(75) Inventor: Richard J. Mackool, Astoria, NY (US)

(73) Assignee: Novartis AG (CH)

( * ) Notice: Subject to any disclaimer, the term of this patent is extended or adjusted under 35 U.S.C. 154(b) by 1189 days.

(21) Appl. No.: 12/984,196

(22) Filed: Jan. 4, 2011

(65) Prior Publication Data

US 2011/0106096 A1 May 5, 2011

Related U.S. Application Data

(63) Continuation of application No. 12/350,294, filed on Jan. 8, 2009, now Pat. No. 8,423,126, which is a continuation of application No. 10/353,431, filed on Jan. 29, 2003, now abandoned.

(51) Int. Cl.

| A61B 6/00 | (2006.01) |
|---|---|
| A61F 9/007 | (2006.01) |
| A61B 17/32 | (2006.01) |
| A61B 17/00 | (2006.01) |

(52) U.S. Cl.
CPC ..... *A61F 9/00745* (2013.01); *A61B 17/320068* (2013.01); *A61B 2017/00066* (2013.01); *A61B 2017/00084* (2013.01)

(58) Field of Classification Search
USPC ........ 600/472, 473, 475, 476; 606/12, 27, 28, 606/31
See application file for complete search history.

(56) References Cited

U.S. PATENT DOCUMENTS

| 4,246,784 | A | * | 1/1981 | Bowen .......................... 374/117 |
|---|---|---|---|---|
| 4,954,960 | A | * | 9/1990 | Lo et al. ........................ 702/124 |
| 5,409,481 | A | * | 4/1995 | Poppas et al. .................. 606/12 |
| 5,505,693 | A | | 4/1996 | Mackool |
| 5,707,369 | A | | 1/1998 | Vaitekunas |
| 5,962,027 | A | * | 10/1999 | Hughes ......................... 424/571 |
| 6,083,193 | A | | 7/2000 | Kadziauskas |

(Continued)

FOREIGN PATENT DOCUMENTS

EP  0988865 A2  3/2000

OTHER PUBLICATIONS

Uday Devgan, MD, FACS, "Decreasing Phaco Energy Optimizing surgical parameters in the age of refractive cataract surgery", Insert to Cataract & Refractive Surgery Today, Nov./Dec. 2004, pp. 30-34.

(Continued)

*Primary Examiner* — James Kish
(74) *Attorney, Agent, or Firm* — Hess Patent Law Firm LLC; Robert J. Hess

(57) ABSTRACT

A method and apparatus to operate a surgical instrument in response to a thermal condition being detected that warrants curtailment of further operation. When the thermal condition is reached, command signals are generated that cause a needle of the surgical instrument to either have its vibrational speed slowed, have its vibrational movement stopped, or have it withdrawn from its relative position. The detection is of infrared radiation wavelengths and is carried out with either a thermal imaging device of a thermal recognition device. A corresponding temperature of the detected infrared radiation wavelengths is compared to a critical temperature to determine whether the thermal condition has been reached.

6 Claims, 2 Drawing Sheets

(56) References Cited

U.S. PATENT DOCUMENTS

| | | | |
|---|---|---|---|
| 6,213,998 B1* | 4/2001 | Shen et al. | 606/10 |
| 6,392,814 B1* | 5/2002 | Ono | 359/661 |
| 6,533,780 B1* | 3/2003 | Laird et al. | 606/41 |
| 7,077,820 B1* | 7/2006 | Kadziauskas et al. | 604/22 |
| 2002/0111608 A1* | 8/2002 | Baerveldt et al. | 606/6 |
| 2003/0199783 A1* | 10/2003 | Bloom et al. | 600/549 |

OTHER PUBLICATIONS

"Infrared detector", Wikipedia, Jan. 2, 2012, http://en.wikipedia.org/wiki/Infrared_detector.

Kevin M. Miller, M.D., Temperature of phaco tips is a function of ultrasound power management and fluid flow, ASCRS Eyeworld, Feb. 2004.

* cited by examiner

MONITORING THERMAL CONDITIONS TO VARY OPERATION OF AN ULTRASONIC NEEDLE TIP OF A SURGICAL INSTRUMENT

CROSS-REFERENCE TO COPENDING PATENT APPLICATIONS

This is a continuation of Ser. No. 12/350,294 filed Jan. 8, 2009 now U.S. Pat. No. 8,423,123, which is a continuation of Ser. No. 10/353,431 filed Jan. 29, 2003, now abandoned.

BACKGROUND OF THE INVENTION

1. Field of the Invention

The present application relates to slowing or stopping the vibratory speed of an ultrasonic needle tip of a surgical instrument during ocular surgery or to withdrawing the needle, depending upon whether a medically unsafe thermal condition is likely to be reached if the ultrasonic needle tip is permitted to continue to vibrate at the same rate of speed and at the same location.

2. Description of Related Art

U.S. Pat. No. 5,409,481 describes a laser tissue welding control that includes monitoring through a surgical microscope and using an infrared radiation wavelength detector, i.e., a pyrometer, to ascertain temperature of a viewed object because the sensed infrared wavelengths are proportional to the temperature of the viewed object. An example of a pyrometer is that of Model M67S produced by Mikron Instrument Co.

U.S. Pat. No. 5,505,693 (the '693 patent) describes an invention that reduces heat generation during ocular surgery from giving rise to an medically unsafe thermal condition caused by heat generation from frictional effects of a vibratory motion of an ultrasonic needle tip of a surgical instrument acting on surrounding tissue. The normal temperature of body tissues is 37° C., the surface tissue of the eye is normally slightly cooler, typically 35° C., and a temperature of approximately 55° C. or greater can cause damage to ocular tissue.

In a worst-case scenario of an ultrasonic transducer, driver and needle with a mass of 23 grams, a frequency of 60 KHz and a stroke length of 0.004 inches, the following calculation can be made. Ultrasonic power is approximately 32 Joules/second. If 80% of this energy is dissipated on the sleeve(s), the heat energy released would be 6 calories/second. Assuming that the area of a sleeve in contact with the tissue is 15-20 square millimeters and that a 3 mm thick region of tissue surrounding the sleeve accepts all the heat, temperature rise (in this region of tissue) would be 10°.-14° C./second. Within this region of tissue and fluids, there will exist a temperature gradient, with the tissue in direct contact with the sleeve having the highest temperatures, and that most separated from direct sleeve contact experiencing lesser temperature elevations.

Under these circumstances, the approximate 55° C. or greater limit would be reached in 1.5-2.0 seconds of full-power application by the ultrasonic transducer. In accordance with the invention, a dynamic friction coefficient of 0.1 between the outer needle surface and the inner sleeve surface will reduce heat generation by 90%, and will allow at least 15-20 seconds of operation before a tissue temperature of approximately 55° C. or greater limit is reached.

It would be desirable to prevent a medically unsafe thermal condition from being reached while operating a vibratory needle of a surgical instrument.

SUMMARY OF THE INVENTION

One aspect of the invention resides in detecting an infrared radiation wavelength with a thermal imaging or thermal recognition source, evaluating whether a critical temperature has been reached based on the detecting, and, if so, generating appropriate command signals to either slow or stop the needle vibratory speed or withdraw the needle from its relative position.

Another aspect of the invention resides in carrying out the detecting of infrared radiation wavelengths at a location along the surgical instrument other than at the needle tip, such as proximal to the needle tip, at the needle hub or at the needle driver.

BRIEF DESCRIPTION OF THE DRAWING

For a better understanding of the present invention, reference is made to the following description and accompanying drawings, while the scope of the invention is set forth in the appended claims:

DETAILED DESCRIPTION OF THE INVENTION

The subject matter of the '693 patent is incorporated by reference. The present invention broadens and amplifies that subject matter with respect to providing infrared radiation wavelength detection, evaluating same with respect to a critical temperature, and issuing appropriate command signals.

Figure 1:
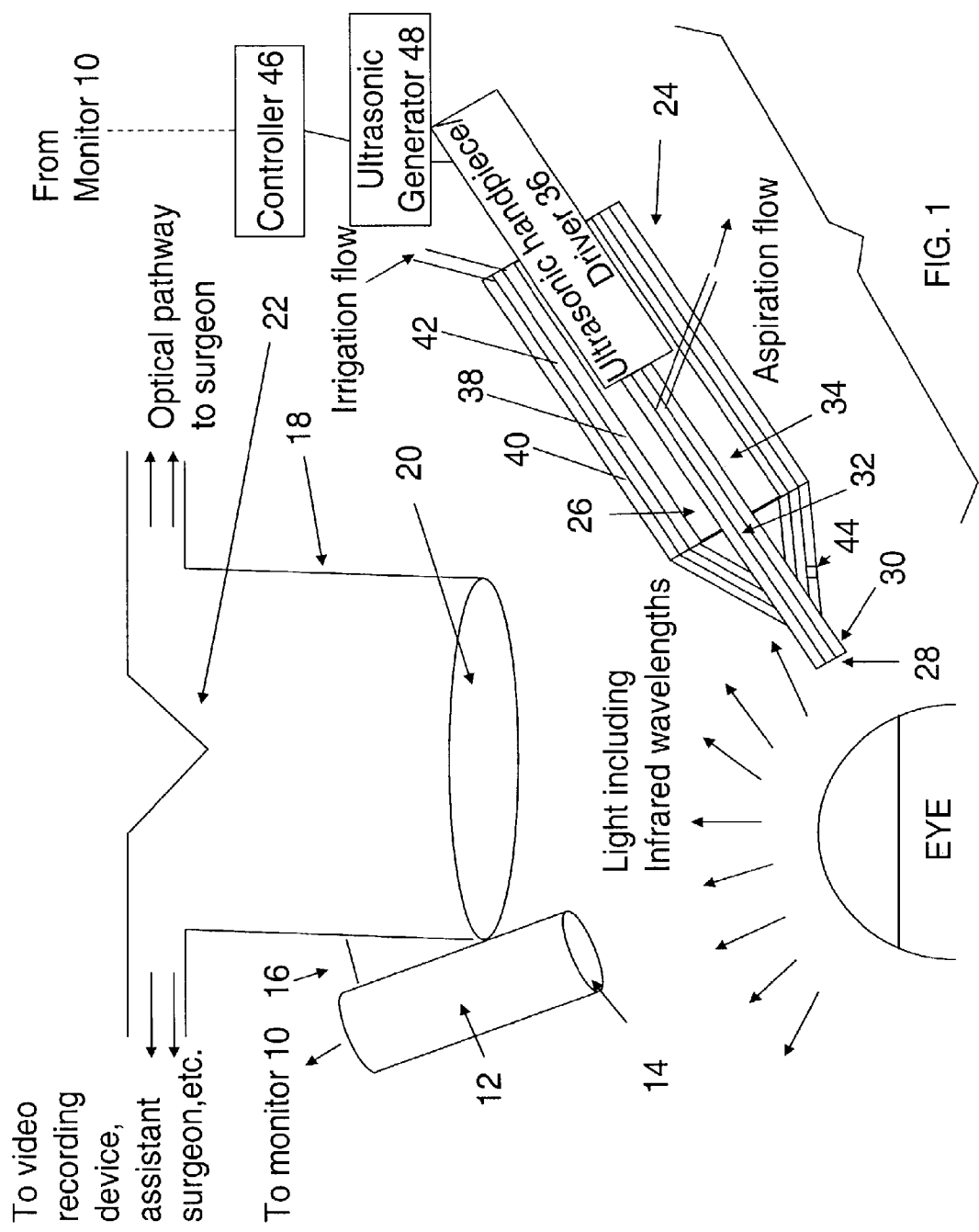
FIG. 1 is a schematic representation of a thermal imaging or thermal recognition source, surgical operating microscope and surgical instrument in accordance with the invention.
Figure 2:
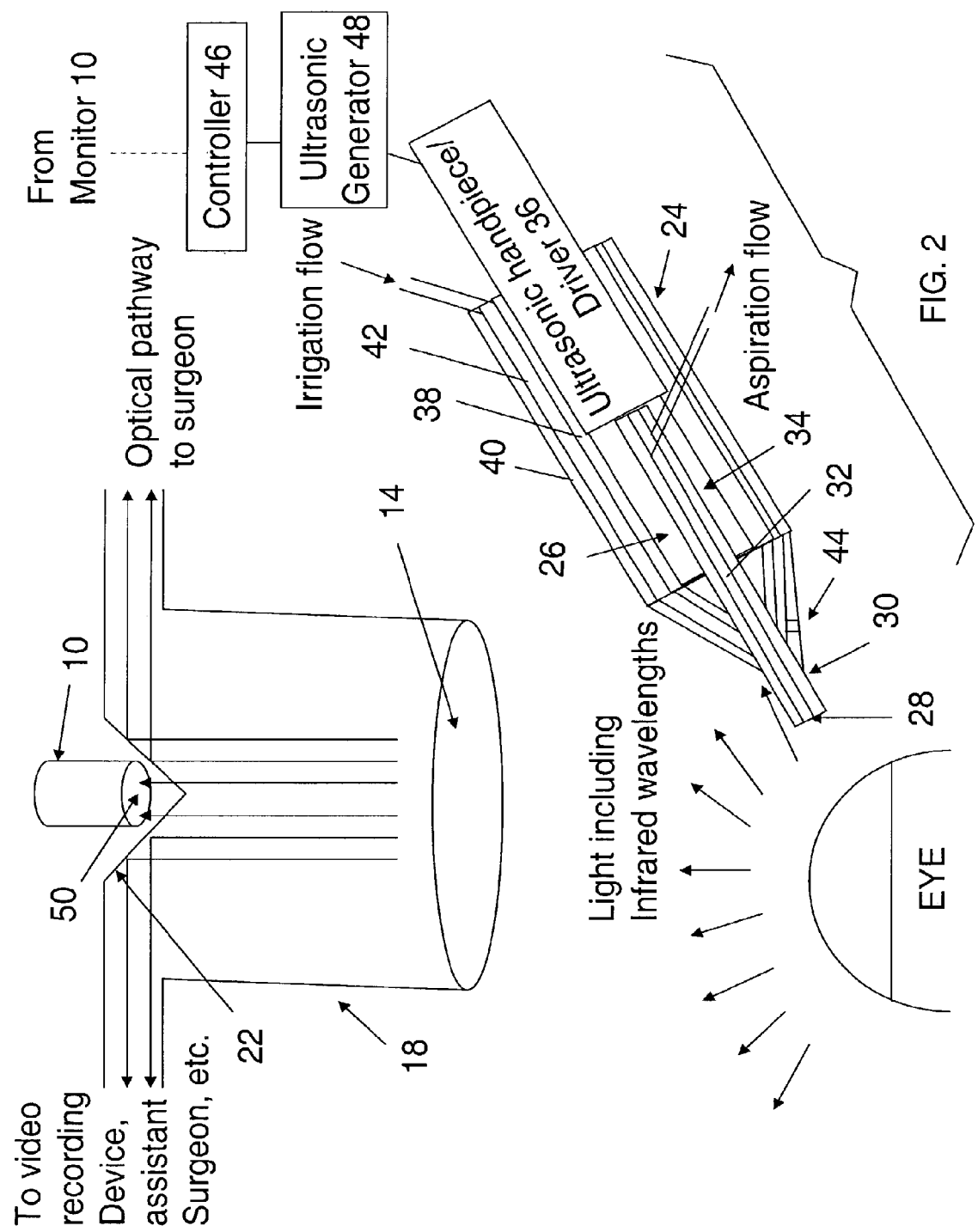
FIG. 2 is a schematic representation as in FIG. 1 but of a further embodiment.

Turning to FIGS. 1 and 2, two embodiments are depicted. Each shows a monitor 10, a surgical operating microscope 18 and a surgical instrument 24. They differ with respect to the location of the monitor 10 and the components that direct the light, including infrared wavelengths, from a heat source to be monitored such as a surgical field in the eye.

The monitor 10 may be a thermal imaging or thermal recognition source, such as a conventional thermal imaging camera or optical pyrometer, which is exemplified in U.S. Pat. No. 5,409,481, whose contents are incorporated by reference.

Turning to FIG. 1, the monitor 10 may detect the infrared wavelengths passing through an attachment tube 12. The attachment tube 12 has a lens 14 that collimates the light entering the tube 12. The tube 12 is attached via conventional fasteners 16 to the surgical operating microscope 18 so as to be aimed at the same location as that of the surgical operating microscope 18. The light travels through the tube 12 to reach the monitor 10, which may be an optical pyrometer or thermal imaging camera. The monitor 10 may be equipped with its own further lens (not shown) to focus the collimated light emerging from the tube 12.

In a conventional manner, the surgical operating microscope 18 has a lens 20 that collimates the light that passes through. Such light reflects off an optical beam splitter 22, which splits and directs the light in two directions; along an optical pathway to the surgeon and along an optical pathway to a conventional video recording device.

Turning to FIG. 2, the beam splitter 22 may be configured to allow the light to reflect, as in the embodiment of FIG. 1, and pass through the beam splitter 22 to reach the monitor 10. Alternatively, the monitor may be arranged within the optical pathway to the surgeon or to the video recording device. Indeed, an additional beam splitter may be arranged in such an optical pathway to reflect the infrared radiation wavelengths to the monitor 10 in a manner as described in U.S. Pat. No. 5,409,481, whose contents are incorporated by reference.

As concerns the embodiments of both FIGS. 1 and 2, the monitor 10 is automatically/desirably directed at the location where the heat arises due to the surgical instrument operation. That is, whenever the microscope is aimed at the surgical instrument, the attachment 12 is aimed in a like manner in unison with that of the surgical instrument.

If the monitoring is done through the optical channels or pathways of the microscope 18 as in the embodiment of FIG. 2, the objective lens(es) 14 of the microscope may need to be modified to be more transmissive of the infrared wavelengths that must be monitored. For example, the typical glass or fused silica used in microscopes might need to be changed to a quartz or other material known to transmit infrared radiation well.

The contents of U.S. Pat. No. 5,409,481 are incorporated herein by reference with respect to an infrared radiation detector or pyrometer used in conjunction with the surgical microscope to view and monitor an object whose temperature is to be ascertained. Also, the optical beam splitters of the present invention may be any conventional type such as that disclosed in U.S. Pat. No. 5,409,481 that is incorporated by reference.

The detected infrared wavelengths are proportional to a corresponding temperature that is compared to the critical temperature or critical change in the temperature. The critical temperature or critical change in temperature may constitute a demarcation of temperature ranges between those below that are medically safe for tissue to achieve and those above that risk and therefore being medically unsafe for tissue to achieve. When such a critical temperature or critical change in temperature is reached, an evaluation of such a thermal condition is made so that appropriate command signals may be generated by a controller 46 to a ultrasonic handpiece containing the needle driver 36 of a surgical instrument 24.

A conventional surgical instrument 24 to effect phacoemulsification is shown in FIGS. 1 and 2. It includes a needle 26 having a suction port 28 at its tip 30, an aspiration flow passage 32 within a hub 34 that permits an aspiration flow from the suction port 28 to a discharge, which may be attached to a suction device (not shown) such as a vacuum.

The needle 26 is driven to vibrate at ultrasonic speeds in a conventional manner by a surgical handpiece/driver 36 so as to break up tissue (such as cataract) to be suctioned through the aspiration flow passage 32. An optional elongated inner sleeve 38 and an optional elongated outer sleeve 40 are concentrically arranged about the needle 26 to extend along the length of the needle 26, although such sleeves are not required for practicing the present invention. A gap 42 is formed between the inner and outer sleeves 38, 40 to allow for an irrigation flow to emerge through one or more of the irrigation ports 44. The surgical handpiece/driver 36 responds to command signals from an ultrasonic generator 48 to drive the needle 26 at a particular speed, such as ultrasonic, or to slow down or stop altogether. The monitor 10 may have a focusing lens 50 to focus the collimated light from the microscope lens 14 as shown in FIG. 2 or may be attached to the attachment tube 12 of FIG. 1.

The ultrasonic generator 48 receives direction form a controller 46, which evaluates sensed detection signals from the monitor 10 to determine whether the needle needs to be slowed, stopped or withdrawn based on the sensed detection signals and issue appropriate command signals to the ultrasonic generator 48 to drive the needle 26 accordingly. If desired, two or more critical temperatures may be used to compare with the temperature corresponding to the sensed infrared radiation wavelengths. If the corresponding temperature matches the lower critical temperature(s), the speed of vibration of the needle would be slowed. If the corresponding temperature matches the highest critical temperature, either the needle would need to be stopped from vibrating or be withdrawn.

The monitor 10 may be configured to send the detection signals electronically to the controller 46 and/or audibly and/or visually to the physician to signify the thermal condition sensed. The controller 46 may respond by emitting detection signals that are indicative of the thermal condition sensed. Alternatively, the controller 46 may respond to an absence of signal generation as signifying that the thermal condition has been achieved.

Alternatively, the critical temperature may be a temperature sufficiently close to the medically unsafe temperature that prompt cessation or lowering of the amount of heat generation will avoid actually reaching the medically unsafe temperature, but the critical temperature is still at a medically safe level for surrounding tissue.

If the detected infrared wavelengths are correlated to a change in temperature, then by comparing this change in temperature with a critical change in temperature (corresponding to attaining the afore-mentioned critical temperature), a signal would generate that signifies that such a critical change in temperature had been achieved in a manner that is the same as for the previous discussion concerning achievement of the critical temperature.

The '693 patent calls for monitoring the temperature on the outer surface of the ultrasonic needle. However, I have conducted experimentation that indicates that the greatest temperature elevation may actually occur proximal to the tip of the needle 26, such as along its hub 34 or even in the ultrasonic handpiece/metallic "driver" 36 to which the needle is attached (the ultrasonic handpiece/driver 36 is in turn connected to the ultrasonically vibratable material which is either a piezoelectric crystal or metallic, i.e., nickel).

The elevated temperature in either the ultrasonic handpiece/driver 36 or the needle hub 34 can rapidly spread to the needle tip 30 (and thus to the tissues of the eye that surround the needle tip 30). Therefore, monitoring the former areas should be done and the operation of the surgical instrument 24 should be modified to respond to temperature elevation in these regions (or even more simply to respond to the greatest temperature detected at any location within the surgical field) by discontinuing the ultrasonic vibration if a certain critical temperature is reached.

The surgical instrument includes an optional outer sleeve 40, an optional inner sleeve 38 and a gap 42 between the outer and inner sleeves 38, 40 through which irrigation flow is directed to emerge through an irrigation port 44 in the vicinity of the surgical field close to needle tip 30. The needle tip 30 has a suction port 28 to create an aspiration flow through an aspiration passage 32 from the surgical field to an aspiration port for removal of cataract tissue or the like.

The controller 46 generates command signals to the ultrasonic handpiece/driver 36 to fix the "stroke length" and thus speed of vibration of the needle 26, such as in accordance with a pre-set program. The needle 26 may vibrate at ultrasonic speeds. The controller 46 also generates command signals when warranted to slow or stop the needle 26 and the ultrasonic handpiece/driver 36 responds accordingly to carry out the instructions to slow (reduce the "stroke length") or stop the needle vibration.

Instead of issuing command signals to slow or stop the needle, the needle tip 30 may simply be withdrawn from its position so it no longer creates any friction with surrounding tissue that further heats the area. Such withdrawal may be done in one of two ways. One way is done manually by the surgeon who receives an indication that the detected temperature has reached a critical temperature. Upon learning of this thermal condition, the surgeon then withdraws the surgical instrument 24 so that the tip 30 does not continue to rub against tissue that results in frictional heating effects. Another method would utilize a needle that is retractable from its extended position where its tip 30 protrudes outward from the surgical instrument 24 to a retracted position where the tip 30 is withdrawn into the surgical instrument 24, the controller 46 may generate command signals to an appropriate device that may cause the ultrasonic handpiece/driver 36 to retract the needle even though the needle may or may not continue to vibrate at its set speed.

If the ultrasonic handpiece/driver 36 is incapable of retracting the needle 26, the needle 26 may be spring biased (not shown) into a retracted position such that its tip no longer protrudes. Command signals from the controller 46 may trigger a latch mechanism (not shown) to release the spring and thereby allow the needle to retract. To restore the needle to its extended position, the needle would be pushed, for instance manually, against the spring bias until latched into its extended position.

Once the needle speed is stopped due to the attainment of a thermal condition corresponding to the critical temperature condition, irrigating the surgical site cools it within seconds sufficiently to lower the temperature. The drop in temperature may be monitored until it reaches a sufficiently low temperature that the needle may resume vibration without risk of again achieving the thermal condition too quickly so that the physician is unable to work on the surgical site for a medically desired time period. If desired, the lower temperature that must be achieved before the needle will be permitted to vibrate again may be that of the original starting temperature before the temperature rose to attain the thermal condition corresponding to that of the critical temperature condition.

While the foregoing description and drawings represent the preferred embodiments of the present invention, it will be understood that various changes and modifications may be made without departing from the spirit and scope of the present invention.

The invention claimed is:

1. A method of fixing needle stroke length of a vibrating hollow needle of a surgical instrument and or slowing or stopping the hollow needle, comprising the steps of:
performing phacoemulsification with a surgical instrument having a driver and a hollow needle;
detecting an infrared radiation wavelength emanating from a location with a monitor during the performing of the phacoemulsification, selecting the monitor from the group consisting of a thermal imaging source and a thermal recognition source; and
evaluating the detected infrared radiation wavelength with a controller to make a determination as to whether the hollow needle needs to be slowed or stopped, the controller fixing a stroke length of the hollow needle and thus a speed of vibration of the hollow needle based on the evaluated, detected infrared radiation wavelength and sending appropriate command signals to the driver so that the hollow needle vibrates and travels in accord with the fixed stroke length, the controller sending further command signals to the driver as warranted based on the evaluated, detected infrared radiation wavelength to slow or stop the hollow needle;
wherein the determination as to whether the hollow needle needs to be slowed or stopped is based on a comparison of critical temperatures with a temperature that corresponds to the detected infrared radiation wavelength, and
wherein the comparison compares at least two different critical temperatures with the corresponding temperature that corresponds to the detected infrared radiation wavelength, the generated command signals signifying direction to fix the needle stroke length so as to slow a speed of vibration of the hollow needle if the corresponding temperature matches a lower one of the at least two different critical temperatures and so as to stop or withdraw the hollow needle if the corresponding temperature matches a higher one of the at least two different critical temperatures.

2. A method of fixing needle stroke length of a vibrating hollow needle of a surgical instrument and or slowing or stopping the hollow needle, comprising the steps of:
performing phacoemulsification with a surgical instrument having a driver and a hollow needle;
detecting an infrared radiation wavelength emanating from a location with a monitor during the performing of the phacoemulsification, selecting the monitor from the group consisting of a thermal imaging source and a thermal recognition source; and
evaluating the detected infrared radiation wavelength with a controller to make a determination as to whether the hollow needle needs to be slowed or stopped, the controller fixing a stroke length of the hollow needle and thus a speed of vibration of the hollow needle based on the evaluated, detected infrared radiation wavelength and sending appropriate command signals to the driver so that the hollow needle vibrates and travels in accord with the fixed stroke length, the controller sending further command signals to the driver as warranted based on the evaluated, detected infrared radiation wavelength to slow or stop the hollow needle;
wherein the determination as to whether the hollow needle needs to be slowed or stopped is based on a comparison of critical temperatures with a temperature that corresponds to the detected infrared radiation wavelength, and
wherein the critical temperatures are at a medically safe level for surrounding tissue yet sufficiently close to a medically unsafe temperature to prompt cessation or lowering of an amount of heat generation to avoid actually reaching the medically unsafe temperature.

3. A method of fixing needle stroke length of a vibrating hollow needle of a surgical instrument and or slowing or stopping the hollow needle, comprising the steps of:
performing phacoemulsification with a surgical instrument having a driver and a hollow needle;
detecting an infrared radiation wavelength emanating from a location with a monitor during the performing of the phacoemulsification, selecting the monitor from the group consisting of a thermal imaging source and a thermal recognition source; and
evaluating the detected infrared radiation wavelength with a controller to make a determination as to whether the hollow needle needs to be slowed or stopped, the controller fixing a stroke length of the hollow needle and thus a speed of vibration of the hollow needle based on the evaluated, detected infrared radiation wavelength and sending appropriate command signals to the driver so that the hollow needle vibrates and travels in accord with the fixed stroke length, the controller sending further command signals to the driver as warranted based on the evaluated, detected infrared radiation wavelength to slow or stop the hollow needle;

wherein the location is at a driver of the hollow needle that drives the hollow needle to vibrate and travel the fixed stroke length.

4. An apparatus to fix needle stroke length of a vibrating hollow needle of a surgical instrument and to slow or stop the hollow needle, comprising:

a surgical instrument suited to perform phacoemulsification, the surgical instrument having a driver and having a hollow needle;

a monitor configured and arranged to be aimed to detect an infrared radiation wavelength emanating from a location during performing of the phacoemulsification by the surgical instrument, the monitor being selected from the group consisting of thermal imaging source and a thermal recognition source; and a controller suited to evaluate the detected infrared radiation wavelength to make a determination as to whether the hollow needle needs to be slowed or stopped, the controller having means for fixing the stroke length of the hollow needle and thus a speed of vibration of the hollow needle based upon the evaluated, detected infrared radiation wavelength, the controller having means for sending appropriate command signals to the driver that direct the driver to drive the hollow needle in accord with the fixed stroke length of the hollow needle, the controller having means for sending further command signals to the driver as warranted based on the evaluated, detected infrared radiation wavelength to slow or stop the hollow needle;

wherein the controller bases the determination on a comparison between critical temperatures and a temperature that corresponds to the detected infrared radiation wavelength;

wherein the controller compares at least two different critical temperatures with the corresponding temperature that corresponds to the detected infrared radiation wavelength to make the comparison, the generated command signals signifying direction to fix the needle stroke length so as to slow a speed of vibration of the hollow needle if the corresponding temperature matches a lower one of the at least two different critical temperatures and so as to stop or withdraw the hollow needle if the corresponding temperature matches a higher one of the at least two different critical temperatures.

5. An apparatus to fix needle stroke length of a vibrating hollow needle of a surgical instrument and to slow or stop the hollow needle, comprising:

a surgical instrument suited to perform phacoemulsification, the surgical instrument having a driver and having a hollow needle;

a monitor configured and arranged to be aimed to detect an infrared radiation wavelength emanating from a location during performing of the phacoemulsification by the surgical instrument, the monitor being selected from the group consisting of thermal imaging source and a thermal recognition source; and a controller suited to evaluate the detected infrared radiation wavelength to make a determination as to whether the hollow needle needs to be slowed or stopped, the controller having means for fixing the stroke length of the hollow needle and thus a speed of vibration of the hollow needle based upon the evaluated, detected infrared radiation wavelength, the controller having means for sending appropriate command signals to the driver that direct the driver to drive the hollow needle in accord with the fixed stroke length of the hollow needle, the controller having means for sending further command signals to the driver as warranted based on the evaluated, detected infrared radiation wavelength to slow or stop the hollow needle;

wherein the controller bases the determination on a comparison between critical temperatures and a temperature that corresponds to the detected infrared radiation wavelength;

wherein the critical temperatures are at a medically safe level for surrounding tissue yet sufficiently close to a medically unsafe temperature to prompt cessation or lowering of an amount of heat generation to avoid actually reaching the medically unsafe temperature.

6. An apparatus to fix needle stroke length of a vibrating hollow needle of a surgical instrument and to slow or stop the hollow needle, comprising:

a surgical instrument suited to perform phacoemulsification, the surgical instrument having a driver and having a hollow needle;

a monitor configured and arranged to be aimed to detect an infrared radiation wavelength emanating from a location during performing of the phacoemulsification by the surgical instrument, the monitor being selected from the group consisting of thermal imaging source and a thermal recognition source; and a controller suited to evaluate the detected infrared radiation wavelength to make a determination as to whether the hollow needle needs to be slowed or stopped, the controller having means for fixing the stroke length of the hollow needle and thus a speed of vibration of the hollow needle based upon the evaluated, detected infrared radiation wavelength, the controller having means for sending appropriate command signals to the driver that direct the driver to drive the hollow needle in accord with the fixed stroke length of the hollow needle, the controller having means for sending further command signals to the driver as warranted based on the evaluated, detected infrared radiation wavelength to slow or stop the hollow needle;

wherein the location is at a driver of the hollow needle that drives the hollow needle to vibrate and travel the fixed stroke length.

* * * * *